(12) United States Patent
Mozdzierz et al.

(10) Patent No.: US 11,058,506 B2
(45) Date of Patent: Jul. 13, 2021

(54) FORCE SENSOR FOR SURGICAL DEVICES

(71) Applicant: Covidien LP, Mansfield, MA (US)

(72) Inventors: Patrick Mozdzierz, Glastonbury, CT (US); Anthony Sgroi, Wallingford, CT (US); David Valentine, Hamden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/714,005

(22) Filed: Dec. 13, 2019

(65) Prior Publication Data

US 2020/0113642 A1     Apr. 16, 2020

Related U.S. Application Data

(62) Division of application No. 15/665,789, filed on Aug. 1, 2017, now Pat. No. 10,595,951.

(Continued)

(51) Int. Cl.
| | |
|---|---|
| *G01L 5/00* | (2006.01) |
| *A61B 34/00* | (2016.01) |
| *G01L 1/22* | (2006.01) |
| *A61B 17/115* | (2006.01) |
| *A61B 90/00* | (2016.01) |
| *A61B 17/00* | (2006.01) |
| *A61B 34/20* | (2016.01) |

(52) U.S. Cl.
CPC .......... *A61B 34/76* (2016.02); *A61B 17/1155* (2013.01); *A61B 34/25* (2016.02); *A61B 34/77* (2016.02); *G01L 1/2243* (2013.01); *G01L 1/2268* (2013.01); *G01L 5/0028* (2013.01); *A61B 2017/00017* (2013.01); *A61B 2017/0046* (2013.01); *A61B 2017/00398* (2013.01); *A61B 2017/00473* (2013.01); *A61B 2034/2061* (2016.02); *A61B 2090/064* (2016.02)

(58) Field of Classification Search
CPC ..... A61B 34/25; A61B 34/77; A61B 17/1155; A61B 2034/2061; A61B 2090/064; A61B 2017/00017; A61B 2017/00398; A61B 2017/0046; A61B 2017/00473; G01L 1/2243; G01L 1/2268; G01L 5/0028
USPC .......................................................... 606/130
See application file for complete search history.

(56) References Cited

U.S. PATENT DOCUMENTS

| | | | | |
|---|---|---|---|---|
| 4,311,980 A | * | 1/1982 | Prudenziati | G01L 1/2287 338/2 |
| 6,573,743 B2 | * | 6/2003 | Sato | G01R 31/31727 324/754.07 |

(Continued)

FOREIGN PATENT DOCUMENTS

| | | |
|---|---|---|
| CN | 2529200 Y | 1/2003 |
| CN | 105212979 A | 1/2016 |

(Continued)

OTHER PUBLICATIONS

European Examination Report dated Jun. 16, 2020 issued in corresponding EP Application No. 17186269.1.

(Continued)

*Primary Examiner* — Max H Noori
(74) *Attorney, Agent, or Firm* — Carter, DeLuca & Farrell LLP (57) ABSTRACT

The present disclosure relates to force sensors and force sensor substrates for use with surgical devices.

16 Claims, 5 Drawing Sheets

Related U.S. Application Data (60) Provisional application No. 62/375,012, filed on Aug. 15, 2016.

(56) References Cited

U.S. PATENT DOCUMENTS

| | | | |
|---|---|---|---|
| 10,167,187 B2* | 1/2019 | Tanaka | B81B 3/0072 |
| 2006/0078873 A1* | 4/2006 | Ogawa | B01L 3/502753 |
| | | | 435/4 |
| 2006/0107768 A1* | 5/2006 | Johnson | G01L 1/144 |
| | | | 73/862.628 |
| 2008/0127752 A1* | 6/2008 | Nakano | G01L 1/2206 |
| | | | 73/862.627 |
| 2013/0274562 A1* | 10/2013 | Ghaffari | A61B 5/046 |
| | | | 600/301 |
| 2014/0241843 A1* | 8/2014 | Golda | H01L 21/67144 |
| | | | 414/751.1 |
| 2015/0285695 A1 | 10/2015 | Sato | |
| 2015/0374370 A1 | 12/2015 | Zergiebel et al. | |
| 2015/0374449 A1 | 12/2015 | Chowaniec et al. | |
| 2016/0296234 A1 | 10/2016 | Richard et al. | |
| 2016/0310134 A1 | 10/2016 | Contini et al. | |
| 2017/0086879 A1 | 3/2017 | Williams | |
| 2017/0254795 A1* | 9/2017 | Qian | G01N 33/4833 |
| 2017/0308198 A1* | 10/2017 | Yoon | G06F 3/0445 |
| 2018/0088708 A1* | 3/2018 | Naganuma | G06F 3/0447 |
| 2018/0171854 A1* | 6/2018 | Szczepanski | F01N 11/00 |
| 2018/0188889 A1* | 7/2018 | Hong | G06F 3/03545 |
| 2019/0110747 A1* | 4/2019 | Majerus | G01L 9/0052 |
| 2020/0100859 A1* | 4/2020 | Shen | A61B 18/1492 |

FOREIGN PATENT DOCUMENTS

| | | |
|---|---|---|
| DE | 202010000341 U1 | 5/2010 |
| JP | S361128132 | 6/1986 |

OTHER PUBLICATIONS

Chinese Office Action dated Jun. 2, 2020 issued in corresponding CN Application No. 201710691386.9.

European Search Report dated Dec. 22, 2017 issued in corresponding EP Application No. 17186269.1.

Chinese Office Action dated Nov. 3, 2020 issued in corresponding CN Appln. No. 2017106913869.

* cited by examiner

FORCE SENSOR FOR SURGICAL DEVICES

CROSS-REFERENCE TO RELATED APPLICATIONS

This application is a divisional of U.S. patent application Ser. No. 15/665,789, filed Aug. 1, 2017, which claims the benefit of and priority to U.S. Provisional Patent Application No. 62/375,012 filed Aug. 15, 2016, the entire disclosure of each of which is incorporated by reference herein.

TECHNICAL FIELD

The present disclosure relates generally to surgical devices. More particularly, the present disclosure relates to force sensors for powered surgical devices.

BACKGROUND

Force sensors are known, and there are multiple methods of fabricating these types of sensors. In one method, sensors utilize bonded strain gauges adhered to a flexing substrate within a load path. For example, a simply supported steel beam that is used integral to a load path can have a strain gauge mounted on the beam. The strain gauge is incorporated in a Wheatstone Bridge Circuit configuration and includes an excitation voltage. The circuit is designed to be at balance before deflection (i.e., no load) and the circuit will have a resistance at zero load. During loading, the beam will deflect and the strain gauge will produce a resistance change. This resistance change is a signal that can be converted into a force value imposed on the beam using a signal conditioner. Depending on the type of configuration (e.g., a quarter bridge, a half bridge, a full bridge), the signal will vary and require calibration to obtain the actual force imposed.

Some strain gauges incorporate a thin plastic film with a bonded NiCr (nickel-chromium or nichrome) wire path embedded on the film. When the film is bonded to the beam and the beam is deflected, the NiCr wire will also be subjected to bending causing a deformation of the wire. The deformation of the wire will cause the above mentioned change in electrical resistance.

The flexing substrate must be configured to elastically deform in an elastic region. In the event that the substrate is subjected to permanent deformation, the sensing wire of the strain gauge will be constrained in the deformed state. This will result in inaccurate subsequent readings of the sensor.

Solder connections are typically utilized in a strain gauge circuit, with the wire path of the strain gauge terminating at a pair of solder pads. Other connections are also used, such as laser welding, mechanical forcing of wires to the contact pads, etc.

The solder connections are subject to possible failures if the connections are made in areas of high strain. Such a strain can cause high levels of deformation causing the solder connections to fatigue. Depending on the level of strain, this fatigue can cause failure of the solder pad resulting in a loss of electrical signal rendering the sensor unusable.

If alternate sensors are used, e.g., those fabricated using vapor deposition of brittle materials, this phenomena can become more problematic. Sensor fabricated using vapor deposition include depositing several layers of media to create the sensor. Typically, the first layer consists of a thin layer of glass deposited along a surface that will incorporate the sensing wire. The sensing wire is first deposited along the substrate as a full NiCr covering. A laser then etches away the NiCr until the desired wire path is created having a plurality of solder pads forming a sensing element as described above with respect to the bonded strain gauge. Finally, a covering layer is used to prevent moisture ingress preventing shorts of the wire trace. The covering layer may be a cured epoxy or an RTV sealant (e.g., room temperature vulcanization silicone), or a vapor deposited glass with a region of glass etched away to gain access to the solder pads. This allows for the soldering of the wires or a flex cable to the sensor.

The configurations described above suffer from problems. One problem is the ability to load the substrate in an instrument. When utilizing glass along the substrate, the glass can crack when loaded. Another problem is premature failing due to large strains on the solder pads.

SUMMARY

In one aspect of the present disclosure, a force sensor substrate includes a proximal surface including a proximal load contact area, and a distal surface including at least one distal load contact area and a sensing area. The distal surface is planar and has at least one groove defined therein separating the at least one distal load contact area from the sensing area.

According to another aspect of the present disclosure, a force sensor substrate includes a proximal surface including a proximal load contact area and a distal surface including a distal load contact area and a sensing area. The distal surface is planar and has at least one groove defined in the sensing area.

Embodiments can include one or more of the following advantages:

The force sensors and substrates thereof may be configured to withstand large loading forces without disrupting the surface containing the sensing electronics (e.g., sensing elements or strain gauges, and their associated components).

The force sensors and substrates thereof may be configured to prevent tear propagation of protective conformal coatings and/or layers of sensing elements disposed thereon, and/or prevent surface micro-strain from damaging solder welds.

The force sensors and substrates thereof may be configured to withstand environmental stresses associated with autowashing and/or autoclaving, thereby rendering the force sensors more durable for reuse.

Other aspects, features, and advantages will be apparent from the description, drawings, and the claims.

BRIEF DESCRIPTION OF THE DRAWINGS

Various aspects of the present disclosure are described herein below with reference to the drawings, which are incorporated in and constitute a part of this specification, wherein.

DETAILED DESCRIPTION

Embodiments of the present disclosure are now described in detail with reference to the drawings in which like reference numerals designate identical or corresponding elements in each of the several views. Throughout this description, the term "proximal" refers to a portion of a device, or component thereof, that is closer to a hand of a user, and the term "distal" refers to a portion of the device, or component thereof, that is farther from the hand of the user.

Figure 1:
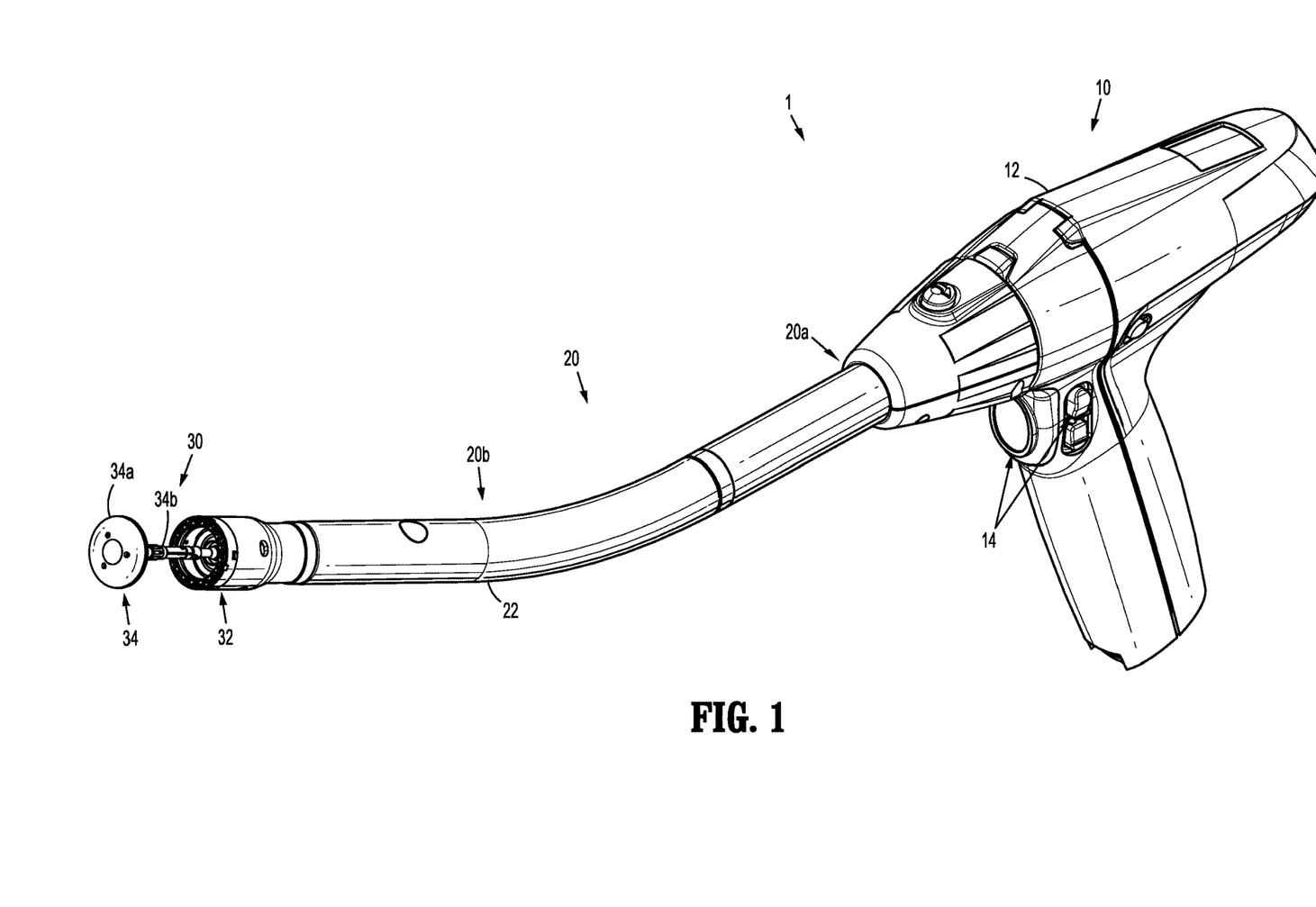
FIG. 1 is a perspective view of a surgical device in accordance with an embodiment of the present disclosure.

Turning now to FIG. 1, a surgical device 1, in accordance with an embodiment of the present disclosure, is in the form of a powered handheld electromechanical instrument, and includes a powered handle assembly 10, an adapter assembly 20, and a tool assembly or end effector 30 including a loading unit 32 having a plurality of staples (not shown) disposed therein and an anvil assembly 34 including an anvil head 34a and an anvil rod 34b. The powered handle assembly 10 is configured for selective connection with the adapter assembly 20 and, in turn, the adapter assembly 20 is configured for selective connection with the end effector 30.

While described and shown as including adapter assembly 20 and end effector 30, it should be understood that a variety of different adapter assemblies and end effectors may be utilized in the surgical device of the present disclosure. For a detailed description of the structure and function of exemplary surgical devices, reference may be made to commonly owned U.S. patent application Ser. No. 14/991,157 ("the '157 application"), filed on Jan. 8, 2016, and Ser. No. 15/096,399 ("the '399 application"), filed on Apr. 12, 2016, the entire contents of each of which are incorporated herein by reference.

With continued reference to FIG. 1, the handle assembly 10 includes a handle housing 12 housing a power-pack (not shown) configured to power and control various operations of the surgical device 1, and a plurality of actuators 14 (e.g., finger-actuated control buttons, knobs, toggles, slides, interfaces, and the like) for activating various functions of the surgical device 1. For a detailed description of an exemplary handle assembly, reference may be made to the '399 application, the entire contents of which was previously incorporated herein by reference.

Figure 2:
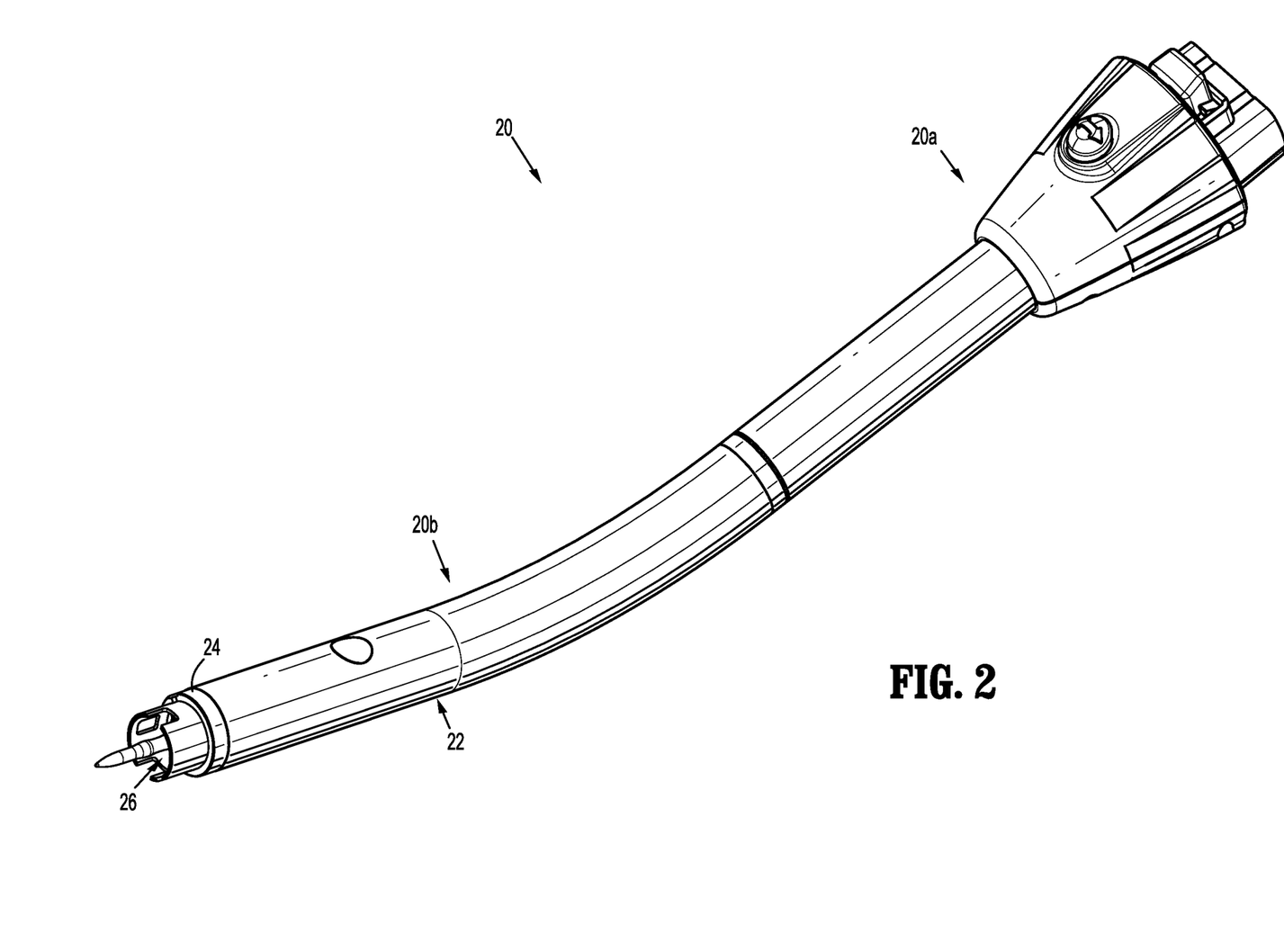
FIG. 2 is a perspective view of an adapter assembly of the surgical device of FIG. 1.

Referring now to FIG. 2, in conjunction with FIG. 1, the adapter assembly 20 includes a proximal portion 20a configured for operable connection to the handle assembly 10 (FIG. 1) and a distal portion 20b configured for operable connection to the end effector 30 (FIG. 1). The adapter assembly 20 includes an outer sleeve 22, and a connector housing 24 secured to a distal end of the outer sleeve 22. The connector housing 24 is configured to releasably secure an end effector, e.g., the end effector 30 (FIG. 1), to the adapter assembly 20.

The adapter assembly 20 will only further be described to the extent necessary to fully disclose the aspects of the present disclosure. For detailed description of an exemplary adapter assembly, reference may be made to the '157 application, the entire contents of which was previously incorporated herein by reference.

Figure 3A:
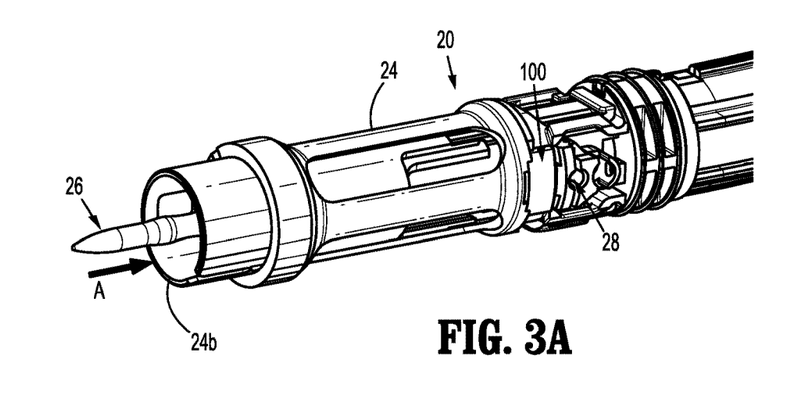
FIGS. 3A and 3B are perspective views of a distal end portion of the adapter assembly of FIGS. 1 and 2, with an outer sleeve of the adapter assembly removed.
Figure 3B:
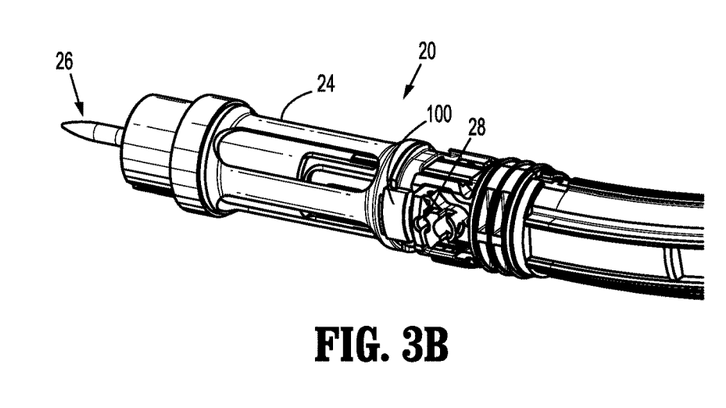
Figure 3C:
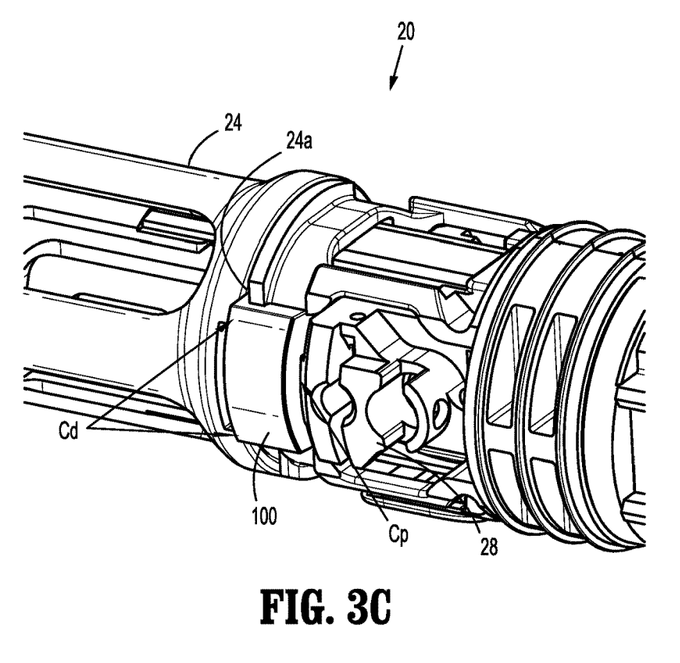
FIG. 3C is an enlarged perspective view of a part of the distal end portion of FIGS. 3A and 3B.

With reference now to FIGS. 3A-3C, the adapter assembly 20 further includes a trocar assembly 26 that extends through a central aperture 101 (FIG. 4B) of a force sensor 100 and a central aperture 29 (FIG. 4A) of a trocar connection housing 28. The trocar connection housing 28 releasably secures the trocar assembly 26 relative to the outer sleeve 22 (FIG. 2) of the adapter assembly 20. For a detailed description of an exemplary trocar connection housing, reference may be made to U.S. patent application Ser. No. 14/865,602 ("the '602 application"), filed on Sep. 25, 2015, the entire contents of which are incorporated herein by reference.

Figure 4A:
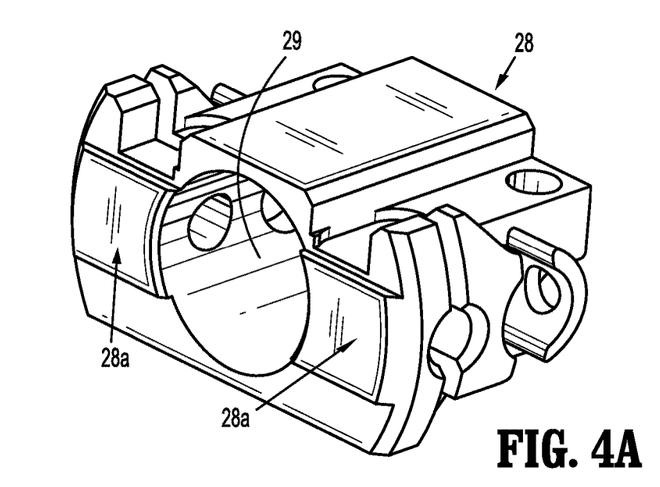
FIG. 4A is a perspective view of a trocar connection housing disposed in the distal end portion of the adapter assembly of FIGS. 3A-3C.
Figure 4B:
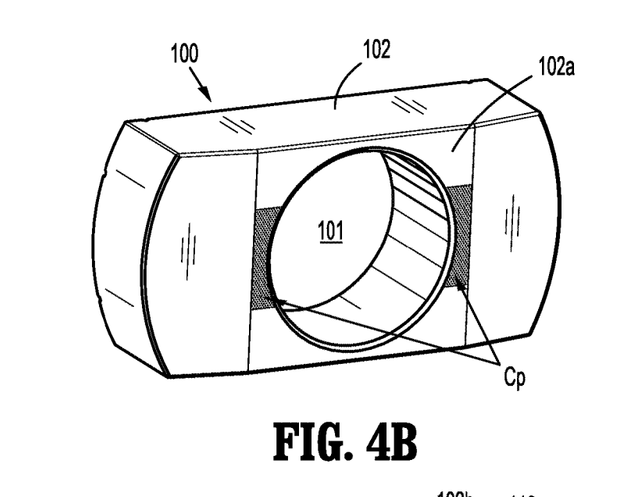
FIGS. 4B and 4C are perspective views of proximal and distal surfaces, respectively, of a substrate of a force sensor disposed in the distal end portion of the adapter assembly of FIGS. 3A-3C.
Figure 4C:
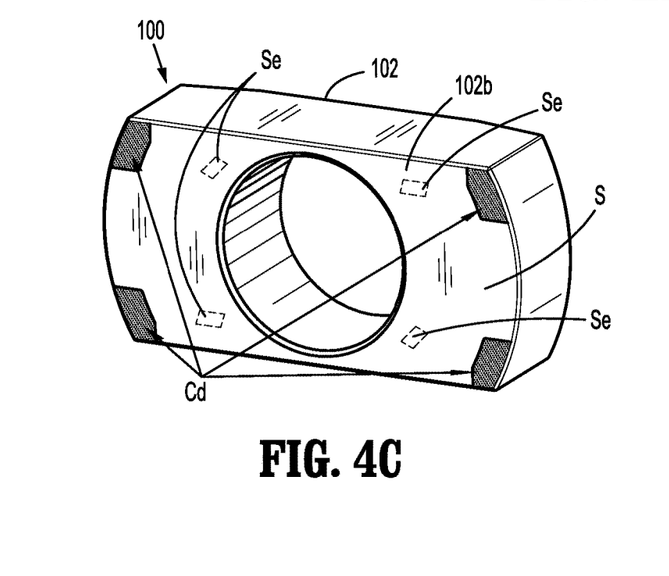

The force sensor 100 is disposed between the trocar connection housing 28 and the connector housing 24 of the adapter assembly 20, and is configured to measure forces along a load path. As shown in FIGS. 4A and 4B, in conjunction with FIG. 3C, the trocar connection housing 28 (FIG. 4A) includes a distal surface 28a which interfaces with, and loads a proximal surface 102a (FIG. 4B) of a body or substrate 102 of the force sensor 100 at proximal load contact areas "Cp". As shown in FIG. 4C, in conjunction with FIG. 3C, a proximal surface 24a (FIG. 3C) of the connector housing 24 defines a contact surface which loads a distal surface 102b of the substrate 102 of the force sensor 100 at distal load contact areas "Cd" (FIG. 4C). Thus, for example, as the anvil assembly 34 (FIG. 1) is approximated towards the loading unit 32 of the end effector 30 during clamping and/or stapling of tissue, the anvil head 34a applies uniform pressure in the direction of arrow "A" (FIG. 3A) against the distal end 24b of the connector housing 24 which, in turn, is transmitted to the distal load contact areas "Cd" of the force sensor 100.

As shown in FIG. 4C, the distal surface 102b of the substrate 102 also defines a sensing area "S" onto which sensing element "Se" (shown in phantom), e.g., strain gauges, are secured. The sensing elements "Se" may be distributed on the distal surface 102b and connected in a variety of configurations, as it within the purview of those skilled in the art.

Figure 5:
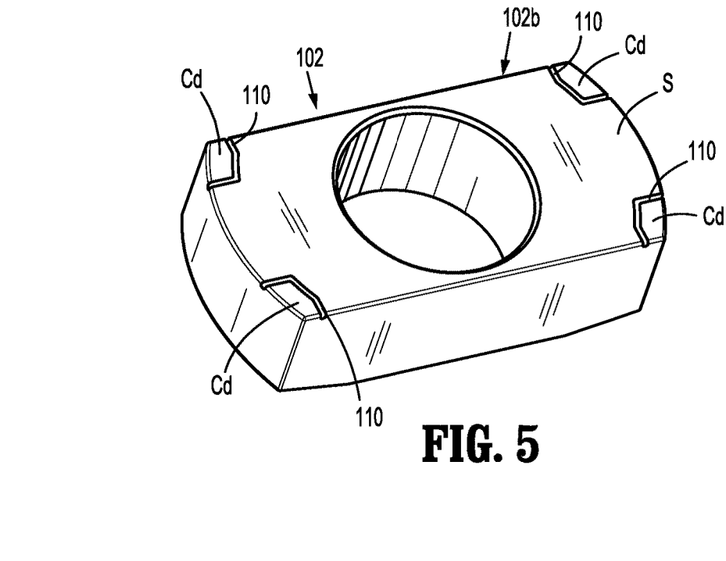
FIG. 5 is a perspective view of the substrate of the force sensor of FIGS. 3A-3C, 4B, and 4C in accordance with an embodiment of the present disclosure.

With reference now to FIG. 5, the distal surface 102b of the substrate 102 is a generally planar surface having a plurality of grooves 110 defined therein. The plurality of grooves 110 provide an area of separation between the distal load contact area "Cd" and the sensing area "S" of the distal surface 102b of the substrate 102. The plurality of grooves 110 may be micro-trenches, relief cuts, among other depressed interruptions formed in the distal surface 102b.

The plurality of grooves 110 may have any width, depth, and/or shape that interrupts the distal surface 102b of the substrate 102. In embodiments, the plurality of grooves 110 have a width of about 0.01 mm and a depth of about 0.01 mm. Moreover, while the plurality of grooves 110 are shown having a rectangular cross-sectional shape, it should be understood that the shape of the plurality of grooves 110 may also vary, e.g., the plurality of grooves 110 may assume a triangular, arcuate, polygonal, uniform, non-uniform, and/ or tapered shape. The plurality of grooves 110 may have any size and geometry that interrupts the distal surface 102b of the substrate 102 to allow, for example, a coating to be masked, cut, or to break without affecting the sensing area "S" of the substrate 102. In embodiments, the plurality of grooves 110 define score lines, tape lines, or break lines in the distal surface 102b of the substrate 102 for coating(s).

The sensing area "S" of the distal surface 102b of the substrate 102 is a flat continuous surface, and the sensing elements "Se" (FIG. 4C) are placed in large strain regions of flex in the sensing area "S." The sensing area "S" of the substrate 102 is free of direct contact with the distal load contacting areas "Cd" via the plurality of grooves 110 thereby minimizing and/or preventing damage to the sensing element "Se" (FIG. 4C) and/or associated components thereof (e.g., layers, coatings, circuitry, solder connections, etc.) as the sensing elements and/or other associated components are not subjected to the direct loading at the distal load contact areas "Cd."

In embodiments in which coatings are utilized to protect the circuitry and/or solder connections (not shown) disposed on the sensing area "S" of the substrate 102, the coatings may terminate at the plurality of grooves 110, without the need for masking processes, thereby minimizing or preventing tearing of the coatings in regions near the distal load contact areas "Cd" during loading of the force sensor 100.

In embodiments in which masking is desired, the plurality of grooves 110 allow for easier masking of the distal load contact areas "Cd" during fabrication of the force sensor 100. The plurality of grooves 110 provide break-away zones in which layers of the sensing elements and/or coatings thereon are forced to break thereby maintaining the integrity of the sensing area "S" of the substrate 102. In embodiments, the plurality of grooves 110 provides a region allowing for easy cutting, e.g., with a knife or razor, to separate the coating from distal load contact areas "Cd."

Figures 6A, 6B, 7A, 7B:
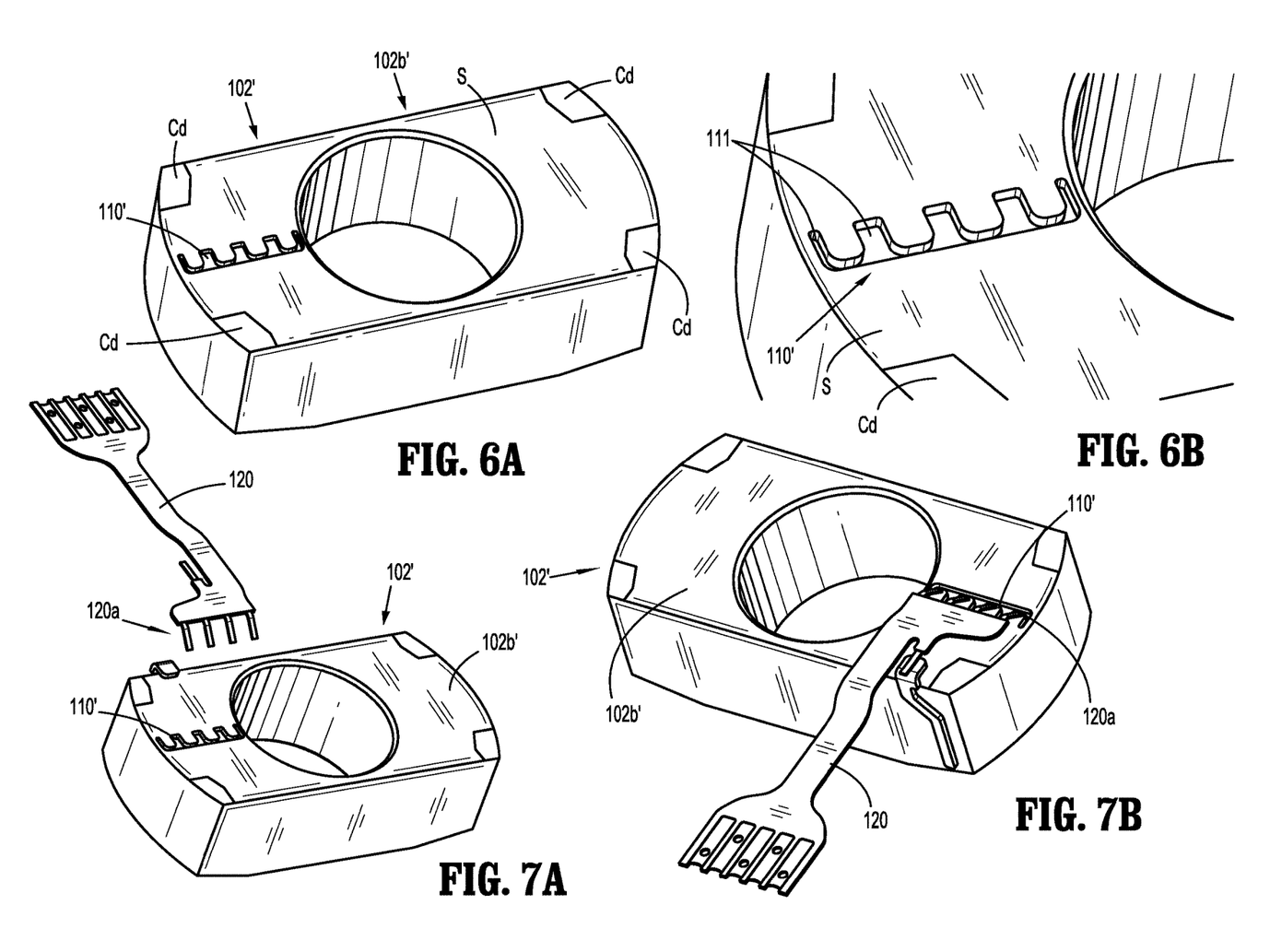
FIG. 6A is a perspective view of a substrate of a force sensor in accordance with another embodiment of the present disclosure.
FIG. 6B is a close-up view of a groove defined in the substrate of FIG. 6A.
FIGS. 7A and 7B are perspective views of the substrate of FIGS. 6A and 6B, including a flex cable and a substrate ground tab.

Referring now to FIGS. 6A and 6B, another embodiment of a force sensor substrate 102' is illustrated. The substrate 102' is similar to substrate 102 and therefore described with respect to the differences therebetween.

The force sensor substrate 102' includes a proximal surface 102a (FIG. 4B) and a distal surface 102b' defining distal load contact areas "Cd" and a sensing area "S". A groove 110' is formed in the sensing area "S" to isolate a desired solder contact surface in the sensing area "S" to create a localized region of reduced strain. The groove 110' includes a series of connected parallel cuts 111, each cut having a peninsula-like configuration. It should be understood, however, that one or more grooves 110' may be formed in a variety of arrangement, e.g., different shapes, depths, and/or widths, to transfer the strain beneath the distal surface 102b' of the substrate 102'.

As shown in FIGS. 7A and 7B, the geometry of the groove 110' corresponds to an end 120a of a flex cable 120, thereby reducing the strain, under load, at the surface of solder joints (not shown) formed between the end 120a of the flex cable 120 and the solder contact surface in the groove 110'. With the reduction of strain at distal surface 102b' of the substrate 102', the integrity of the solder connections are enhanced.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A force sensor comprising:
a substrate including a proximal surface having a proximal load contact area and a distal surface having four distal load contact areas disposed at corners of the substrate and a sensing area, the distal surface being planar and having a plurality of grooves defined therein separating the four distal load contact areas from the sensing area, each groove of the plurality of grooves corresponding to and surrounding one of the four distal load contact areas and terminating at side surfaces of the substrate.

2. The force sensor according to claim 1, wherein the substrate includes a central aperture defined therethrough.

3. The force sensor according to claim 2, wherein the proximal load contact area of the substrate is disposed adjacent to the central aperture.

4. A force sensor comprising:
a substrate including a proximal surface having a proximal load contact area and a distal surface having at least one distal load contact area and a sensing area, the distal surface being planar and having at least one groove defined therein separating the at least one distal load contact area from the sensing area, the at least one groove having a depth of about 0.01 millimeter and a width of about 0.01 millimeter in the distal surface of the substrate.

5. The force sensor according to claim 1, further comprising at least one sensing element disposed on the sensing area of the substrate.

6. The force sensor according to claim 5, wherein the at least one sensing element is a strain gauge.

7. The force sensor according to claim 1, wherein the substrate further includes a groove defined in the sensing area of the substrate.

8. The force sensor according to claim 7, wherein the groove defined in the sensing area includes a series of connected parallel cuts.

9. The force sensor according to claim 4, wherein the substrate includes a central aperture defined therethrough.

10. The force sensor according to claim 9, wherein the proximal load contact area of the substrate is disposed adjacent to the central aperture.

11. The force sensor according to claim 4, wherein the at least one distal load contact area of the substrate includes four distal load contact areas disposed at corners of the substrate.

12. The force sensor according to claim 11, wherein the at least one groove defined in the distal surface of the substrate includes a plurality of grooves, each groove of the plurality of grooves corresponding to and surrounding one of the four distal load contact areas and terminating at side surfaces of the substrate.

13. The force sensor according to claim 4, further comprising at least one sensing element disposed on the sensing area of the substrate.

14. The force sensor according to claim 13, wherein the at least one sensing element is a strain gauge.

15. The force sensor according to claim 4, wherein the substrate further includes a groove defined in the sensing area of the substrate.

16. The force sensor according to claim 15, wherein the groove defined in the sensing area includes a series of connected parallel cuts.

\* \* \* \* \*